United States Patent [19]

Dockner et al.

[11] Patent Number: 5,618,971

[45] Date of Patent: Apr. 8, 1997

[54] SEPARATION OF A MONO(METH)ACRYLATE OF A $C_4$-$C_6$ ALKANEDIOL FROM AN AQUEOUS SOLUTION CONTAINING A MONO(METHACRYLATE) OF A $C_4$-$C_6$ ALKANEDIOL AND THE SAID $C_4$-$C_6$ ALKANEDIOL

[75] Inventors: Toni Dockner, Meckenheim; Helmut Lermer, Ludwigshafen; Ulrich Rauh, Limburgerhof; Gerhard Nestler, Ludwigshafen, all of Germany

[73] Assignee: BASF Aktiengesellschaft, Ludwigshafen, Germany

[21] Appl. No.: 539,771

[22] Filed: Oct. 5, 1995

[30] Foreign Application Priority Data

Oct. 11, 1994 [DE] Germany ............................ 44 36 245.5

[51] Int. Cl.[6] .................................................. C07C 67/48
[52] U.S. Cl. ............................................................. 560/218
[58] Field of Search .............................................. 520/218

[56] References Cited

U.S. PATENT DOCUMENTS 3,162,677  12/1964  Horsley et al. ..................... 560/218

FOREIGN PATENT DOCUMENTS 630187   12/1961  Canada .
0465853  1/1992   European Pat. Off. .
1518572  1/1969   Germany .
4228397  3/1994   Germany .

*Primary Examiner*—Paul J. Killos
*Attorney, Agent, or Firm*—Oblon, Spivak, McClelland, Maier & Neustadt, P.C.

[57] ABSTRACT

A process for the separation of a mono(meth)acrylate of a $C_4$–$C_6$ alkanediol from an aqueous solution containing a mono(meth)acrylate of a $C_4$–$C_6$ alkanediol and the said $C_4$–$C_6$ alkanediol, by extraction with an organic solvent, in which the extracting agent used is an organic solvent selected from the group comprising esters of $C_1$–$C_4$ alkanecarboxylic acids and $C_1$–$C_5$ alkanols, single and mixed dialkyl ethers having from 4 to 8 C atoms, and mixtures of such organic solvents.

10 Claims, No Drawings

SEPARATION OF A MONO(METH)ACRYLATE OF A $C_4$-$C_6$ ALKANEDIOL FROM AN AQUEOUS SOLUTION CONTAINING A MONO(METHACRYLATE) OF A $C_4$-$C_6$ ALKANEDIOL AND THE SAID $C_4$-$C_6$ ALKANEDIOL

The present invention relates to a process for the separation of a mono(meth)acrylate of a $C_4$-$C_6$ alkanediol from an aqueous solution containing a mono(meth)acrylate of a $C_4$-$C_6$ alkanediol and the said $C_4$-$C_6$ alkanediol, by extraction with an organic solvent.

The form "(meth)acryl" is used as abbreviated orthography to stand for "acryl or methacryl".

Mono(meth)acrylates of $G_4$-$C_6$ alkanediols are known (cf eg Ullmanns Encyclopädie der technischen Chemie, "Polyacryl-Verbindungen bis Quecksilber", Vol. 19, 4th Edition, Verlag Chemie (1980), pp. 10). On account of their bifunctionality (hydroxyl group and monoethylenically unsaturated group) they make interesting starting compounds. For example, they are suitable for use as vinyl-unsaturated comonomers in, eg, polymers suitable for use as binding agents and produced by free-radical polymerization. Alternatively, as alcoholic compounds, they are suitable eg for polymerization-type reactions (eg condensation or addition reactions).

It is well known (as disclosed, eg, by DE-PS 1,518,572 und EP-A 465,853) that it is possible to prepare mono(meth)acrylates of $C_4$-$C_6$ alkanediols by direct esterification of (meth)acrylic acid with the appropriate alkanediols in the presence of acid esterification catalysts, with removal of the resulting water by azeotropic distillation using a suitable entraining agent. Since alcohols usually tend, under the influence of acid esterification catalysts, to undergo side reactions such as ether formation, the esterification is preferably carried out using only a small excess of the alkanediol. Under such conditions the formation of the corresponding diesters normally occurs in not inconsiderable amounts, so that the product mixture obtained is usually one which consists substantially of entraining agent, alkanediol, monoester, and diester and from which the desired monoester must be separated.

The desired separation is hampered by the facts that the boiling points of the alkanediol, monoester, and diester are at elevated temperatures even under reduced pressure;

the boiling points of the alkanediol, monoester, and diester are very close together;

the vinyl-unsaturated monoesters and diesters show an increased tendency to undergo polymerization particularly when present in a condensed phase and particularly at elevated temperatures.

When acrylic acid is used as the starting acid and 1,4-butanediol is the alkanediol, the relevant boiling points under standard pressure conditions (1 atm) are, for example, 1,4-butanediol: 230° C. (Roempp, Chemie Lexikon, 9th Edition, Thieme Verlag, Stuttgart, 1989);

1,4-butanediol monoacrylate: ca 230° C. (Technische Information TI/ED 1331 d (1987), published by BASF Aktiengesellschaft);

1,4-butanediol diacrylate: ca 225° C. (Ullmanns Encyklopädie der technischen Chemie, Vol. 19, Verlag Chemie, Weinheim, 1980, pp. 9).

Under these circumstances any separation by rectification is more or less impossible on economic grounds (cf also DE-OS 4,228,397, pp. 1). In DE-PS 1,518,572 it is recommended to effect separation of the product mixture by admixing the same with water and extracting the diester with an extracting agent in the presence of the aqueous phase. It is preferred to use as extracting agent one which is at the same time suitable as an entraining agent for the esterification, in order to make it possible to recycle the organic extraction phase containing the diester directly to the esterification stage. Otherwise the entraining agent would have to be separated from the reaction mixture, possibly by distillation, prior to use of the extracting agent. Extracting agents which can simultaneously function as entraining agents are aliphatic and cycloaliphatic hydrocarbons having a boiling point of from 65° to 120° c. (at 1 atm), such as hexane, heptane, cyclohexane, or methylcyclohexane—cyclohexane being particularly preferred. The aqueous phase which is produced during said extraction is an aqueous solution consisting substantially of water, alkanediol, and the mono(meth)acrylate of the alkanediol forming the desired product.

Starting from this aqueous solution, separation by rectification into monoester and alkanediol is virtually impossible in view of the said positions of the boiling points of the components. Separation of the water by distillation is conceivable, but this process would produce a monoester contaminated with alkanediol, which would be less useful for many applications (for example, alkanediols can have a negative influence on the molecular weight desired in free-radical polymerisations on account of their modifying action, or they can lead to undesirable cross-linking during reactions with diisocyanates).

DE-PS 1,518,572 proposes to solve the problem by separating the monoester from the aqueous solution by extraction with a suitable organic solvent and then removing this extracting agent by distillation. The extracting agent explicitly stated in DE-PS 1,518,572 as being suitable for solving this problem in a satisfactory manner is exclusively methylene chloride. A disadvantage of the use of methylene chloride is, however, the fact that it is not toxicological harmless.

In EP-A 465,853 it is recommended to carry out the esterification in the presence of considerable amounts of added preformed diester, in order to minimize by this means the proportion of unconverted alkanediol in the product mixture. Furthermore EP-A 465,853 recommends washing out the catalytically active acid from the product mixture, then directly extracting the diester compound with an appropriate extracting agent in the absence of water, ie as proposed by DE-PS 1,518,572, and subsequently treating the extracting agent so as to wash out the monoester which has passed into it as a result of this method of extraction, with water, and combining the aqueous phase formed during this process with the extraction phase becoming enriched with monoester and recycling the diester to the esterification stage. As regards the aqueous phase containing monoester and small amounts of alkanediol it is recommended merely to separate the low-boiling components by distillation.

A disadvantage of this procedure is the fact that only a monoester contaminated with alkanediol is obtain.

It was thus the object of the present invention to provide a process for the separation of a mono(meth)acrylate of a $C_4$-$C_6$ alkanediol from an aqueous solution containing a mono(meth)acrylate of a $C_4$-$C_6$ alkanediol and the said $C_4$-$C_6$ alkanediol, by extraction with an organic solvent other than methylene chloride but substantially equivalent to methylene chloride in efficiency whilst exhibiting a reduced danger factor.

Accordingly, we have found a process for the separation of a mono(meth)acrylate of a $C_4$–$C_6$ alkanediol from an aqueous solution containing a mono(meth)acrylate of a $C_4$–$C_6$ alkanediol and the said $C_4$–$C_6$ alkanediol, by extraction with an organic solvent, wherein the extracting agent used is an organic solvent selected from the group comprising esters of $C_1$–$C_4$ alkanecarboxylic acids and $C_1$–$C_5$ alkanols, single and mixed dialkyl ethers having from 4 to 8 C atoms, and mixtures of said organic solvents.

Preferred extracting agents for use in the invention are esters of acetic acid or propionic acid and $C_3$–$C_5$ alkanols, in particular $C_4$ alkanols, in particular isobutyl acetate. Other suitable extracting agents are dialkyl ethers having from 4 to 6, preferably 4, C atoms, in particular the ether of methanol and tert-butanol. In addition mixtures of the aforementioned organic solvents are suitable for use as extracting agents in the invention.

The extracting agents to be used according to the invention are distinguished by the fact that their boiling points under standard pressure conditions (usually below 150° C.) differ sufficiently from that of the mono(meth)acrylate to be taken up by extraction, which guarantees simple distillative separation of the organic extracting agent thereafter.

Furthermore, their extracting action on the mono(meth)acrylates to be taken up is substantially equivalent to that of methylene chloride. That is to say, given the use of identical volumes of extracting agents, they are capable of taking up substantially the same equilibrium amount of monoester from an aqueous solution containing a mono(meth)acrylate of a $C_4$–$C_6$ alkanediol as can methylene chloride, when brought into contact with such a solution at 25° c.

Another favorable aspect of the process of the invention is the fact that the extracting agents to be used in accordance with the invention have the ability to select between the $C_4$–$C_6$ alkanediol and its mono(meth)acrylate to an extent comparable to that shown by methylene chloride.

Moreover, the solubility of the extracting agent to be used according to the invention in water is low to an extent similar to that of methylene chloride, which minimizes the migration of extracting agent to the aqueous solution.

The same relationship applies to the solubility of water in the extracting agents to be used according to the invention and in methylene chloride respectively.

In other words, the extracting agents to be used according to the invention are, surprisingly, capable of replacing the methylene chloride proposed in the prior art for the same purpose whilst showing substantially the same degree of efficiency.

When carrying out the process described in DE-PS 1,518, 572 for the preparation of a mono(meth)acrylate of a $C_4$–$C_6$ alkanediol, frequently aqueous solutions are formed which contain more than 0–15 wt % of $C_4$–$C_6$ alkanediol, more than 0–15 wt % of mono(meth)acrylate of a $C_4$–$C_6$ alkanediol, not more than 3 wt % of other compounds (eg (meth)acrylic acid, catalytic acid, diester, polymerisation inhibitor, etc.) and remainder: water.

The process of the invention is suitable in particular for the extractive separation the mono(meth)acrylate of a $C_4$–$C_6$ alkanediol from such solutions as those mentioned above.

This applies in particular to cases in which the aqueous solution has been formed as the result of a corresponding esterification of 1,4-butanediol and/or 1,6-hexanediol. The latter statement is particularly true when the relevant acid is acrylic acid.

Of course, the process of the invention is also suitable for the extractive separation of mono(meth)acrylates of a $C_4$–$C_6$ alkanediol from a solution containing water and $C_4$–$C_6$ alkanediol, in addition to the aforementioned monoester, as is produced in the process for the synthesis of mono(meth)acrylates of $C_4$–$C_6$ alkanediols described in EP-A 465,853.

Usually the process of the invention will be carried out at a temperature of from 10° to 60° C. and preferably from 20° to 40° C. and more preferably from 20° to 30° C. With increasing temperature the probability of side reactions increases. The slight heat generated during the extraction according to the invention is of minor significance. Normally the extraction according to the invention is carried out under standard pressure conditions (1 atm). It can alternatively be effected under elevated pressure conditions (not more than 15 atm operating pressure).

The extraction according to the invention can be applied, surprisingly, to acidic, neutral, or basic aqueous starting solutions without the occurrence of any appreciable losses of extracting agent as used in the invention, although said extracting agents are sensitive to, eg, hydrolysis or similar side reactions.

Usually the aqueous starting solution will contain the catalytic acid employed during the esterification. Some of it will pass into the organic extraction phase and remain therein during the separation, by distillation, of the extracting agent. If such acidic contaminations are undesirable in the required mono(meth)acrylates, they can be washed out with, say, water or an aqueous base.

Conventional extracting equipment is suitable for carrying out the extraction of the invention, packed columns being particularly preferred. In said equipment, the extracting agent and aqueous solution are passed preferably countercurrently, advantageously the phase of greater specific gravity being fed to the head of the column. Of course, the process step of the invention is carried out, like all other process steps involved in the isolation of mono(meth)acrylates of a $C_4$–$C_6$ alkanediol, in the presence of usual amounts of conventional polymerization inhibitors. This was also the case in the examples below. Suitable polymerization inhibitors to be used in this way are phenothiazine, hydroquinone and, in particular, hydroquinone monomethyl ether.

EXAMPLES (All process steps were carried out in the presence of usual amounts of polymerization inhibitors)

100 mL of an acid aqueous solution, which contained 6 wt % of 1,4-butanediol, 8 wt % of 1,4-butanediol monoacrylate, less than 3 wt % of other compounds and remainder: water and which was produced during the preparation of 1,4-butanediol monoacrylate according to the procedure described in DE-PS 1,518,572, was brought into intimate contact with, in each case, 100 mL of different extracting agents at 25° C. and a pressure of 1 atm. On completion of the phase separation there were determined, in a state of extraction equilibrium:

a) the solubility of the extracting agent in the aqueous phase (SE, given in percent by weight based on the aqueous phase);

b) the solubility of water in the organic phase (SW, given in percent by weight based on the organic phase);

c) the extractive efficiency with respect to 1,4-butanediol monoacrylate, the extractive efficiency of methylene chloride (with respect to the amount of 1,4-butanediol monoacrylate dissolved in methylene chloride) being arbitrarily assigned the value of 100 (EE);

d) the selectivity of the extracting agent (S); in order to determine S, the organic phase present in a state of extraction equilibrium was analyzed by gas chromatography, and in simple manner the ratio, by weight, of the 1,4-butanediol monoacrylate (numerator) to 1,4-butanediol (denominator) (area peaks) was determined as a measure of s.

The following table shows the results obtain for the extracting agents used. It additionally lists the boiling points (Bp. in °C.) at 1 atm.

Virtually no side reactions of the extracting agents used could be discerned.

TABLE

|  | Extracting Agents | | | | |
| --- | --- | --- | --- | --- | --- |
|  | SE | S | SW | EE | Bp |
| methylene chloride | 100 | 97/3 | 2 | 0.14 | 40.2 |
| methyl-tert-butyl ether | 95 | 92/8 | 4.8 | 1.1 | 55.2 |
| isobutyl acetate | 100 | 97/3 | 0.7 | 1.6 | 118 |
| n-butyl acetate | 98 | 95/5 | 0.7 | 1.4 | 126.5 |
| ethyl acetate | 95 | 92/8 | 7.9 | 3.0 | 77.2 |
| methyl propionate | 93 | 90/10 | 0.5 | — | 79.1 |
| toluene (comp. ex.) | 51 | 98/2 | 0.005 | 0.05 | 110.6 |

We claim:

1. A process for the separation of a mono(meth)acrylate of a $C_4$–$C_6$ alkanediol from an aqueous solution containing a mono(meth)acrylate of a $C_4$–$C_6$ alkanediol and the said $C_4$–$C_6$ alkanediol, by extraction with an organic solvent, wherein the extracting agent used is an organic solvent selected from the group comprising esters of $C_1$–$C_4$ alkanecarboxylic acids and $C_1$–$C_5$ alkanols, single and mixed dialkyl ethers having from 4 to 8 C atoms, and mixtures of such organic solvents.

2. A process as defined in claim 1, wherein the extracting agent used is an organic solvent selected from the group comprising esters of acetic acid or propionic acid and $C_3$–$C_5$ alkanols, single and mixed dialkyl ethers having from 4 to 6 C atoms, and mixtures of said organic solvents.

3. A process as defined in claim 1, wherein the extracting agent used is isobutyl acetate, methyl-tert-butyl ether, or a mixture of these two organic solvents.

4. A process as defined in claim 1, wherein 1,4-butanediol or 1,6-hexanediol or a mixture thereof forms the alkanediol.

5. A process as defined in claim 1, wherein the mono(meth)acrylate to be separated is the monoacrylate of 1,4-butanediol, 1,6-hexanediol, or a mixture of these two alkanediols.

6. A process as defined in claim 1, which is carried out at a temperature ranging from 10° to 60° C.

7. A process as defined in claim 1, which is carried at a temperature ranging from 20° to 30° C.

8. A process as defined in claim 1, wherein the aqueous solution contains more than 0–15 wt % of $C_4$–$C_6$ alkanediol, more than 0–15 wt % mono(meth)acrylates of a $C_4$–$O_6$ alkanediol, not more than 3 wt % of other compounds and remainder: water.

9. A process as defined in claim 1, wherein the aqueous solution contains more than 0–15 wt % of 1,4-butanediol, more than 0–15 wt % of 1,4-butanediol monoacrylate, not more than 3 wt % of other compounds and remainder: water.

10. A process for the preparation of a mono(meth)acrylate of a $C_4$–$C_6$ alkanediol by esterification of the (meth)acrylic acid with said alkanediol in the presence of an acidic esterification catalyst with the removal of the resulting water by azeotropic distillation using an entraining agent, extractive separation of the product mixture into an organic solution containing the diester formed as byproduct and an aqueous solution containing the alkanediol used and the mono(meth)acrylate, followed by extractive separation of the mono(meth)acrylate from the aqueous solution containing the alkanediol used and the mono(meth)acrylate, using an extracting agent, followed by separation of the extracting agent and mono(meth)acrylate, wherein the extracting agent used for the extraction of the mono(meth)acrylate from the aqueous phase is an organic solvent selected from the group comprising esters of $C_1$–$C_4$ alkanecarboxylic acids and $C_1$–$C_5$ alkanols, single or mixed dialkyl ethers having from 4 to 8 C atoms, and mixtures of such organic solvents.

* * * * *